United States Patent
LaPointe (10) Patent No.: US 10,393,721 B2
(45) Date of Patent: Aug. 27, 2019

(54) SYSTEMS AND METHODS FOR DETERMINING THE COMPOSITION OF GASEOUS FUEL

(71) Applicant: Cummins, Inc., Columbus, IN (US)

(72) Inventor: Leon A. LaPointe, Columbus, IN (US)

(73) Assignee: Cummins, Inc., Columbus, IN (US)

(*) Notice: Subject to any disclaimer, the term of this patent is extended or adjusted under 35 U.S.C. 154(b) by 137 days.

(21) Appl. No.: 15/503,654

(22) PCT Filed: Aug. 17, 2015

(86) PCT No.: PCT/US2015/045516
§ 371 (c)(1),
(2) Date: Feb. 13, 2017

(87) PCT Pub. No.: WO2016/028685
PCT Pub. Date: Feb. 25, 2016

(65) Prior Publication Data
US 2017/0269051 A1  Sep. 21, 2017

Related U.S. Application Data (60) Provisional application No. 62/039,563, filed on Aug. 20, 2014.

(51) Int. Cl.
*F02B 3/00* (2006.01)
*G01N 33/22* (2006.01)
*G01N 31/12* (2006.01)
*C01B 3/38* (2006.01)
(Continued)

(52) U.S. Cl.
CPC .......... *G01N 33/225* (2013.01); *C01B 3/382* (2013.01); *C01B 3/386* (2013.01); *C10L 3/06* (2013.01);
(Continued)

(58) Field of Classification Search
CPC ... F02B 3/00; F01N 3/023; F01N 3/00; F02M 27/02; F02M 27/00; G01N 33/225;
(Continued)

(56) References Cited

U.S. PATENT DOCUMENTS 4,332,225 A * 6/1982 Cox .................. F02B 77/086
123/697
4,386,858 A   6/1983 Kude et al.
(Continued)

FOREIGN PATENT DOCUMENTS

JP          2001141681 A      5/2001

OTHER PUBLICATIONS

International Search Report and Written Opinion issued for PCT/US2015/045516, dated Nov. 10, 2015, 7 pages.

*Primary Examiner* — Christine T Mui
(74) *Attorney, Agent, or Firm* — Foley & Lardner LLP (57) ABSTRACT

Disclosed are methods, systems, and computer-readable mediums for determining the composition of gaseous fuel. An initial gaseous fuel stream is provided that includes methane, non-methane hydrocarbons, and inert gases. Air is mixed into the initial fuel stream upstream of a first catalyst. The first catalyst oxidizes only the non-methane hydrocarbons of the initial fuel stream to produce a resultant fuel stream comprising methane and inert gases. Air is mixed into the resultant fuel stream downstream of the first catalyst and upstream of a second catalyst. The second catalyst oxidizes only the methane hydrocarbons of the resultant fuel stream to produce an output fuel stream. Mole ratios of the methane, the non-methane hydrocarbons, and the inert gases of the initial fuel stream are each determined.

12 Claims, 7 Drawing Sheets

(51) Int. Cl.
*C10L 3/06* (2006.01)
*F02M 27/02* (2006.01)
*F02M 27/00* (2006.01)

(52) U.S. Cl.
CPC ...... *G01N 31/12* (2013.01); *C01B 2203/0261* (2013.01); *C01B 2203/1235* (2013.01); *C01B 2203/1241* (2013.01); *C01B 2203/142* (2013.01); *C01B 2203/16* (2013.01); *C10L 2290/60* (2013.01)

(58) Field of Classification Search
CPC .......... G01N 33/22; C01B 3/382; C01B 3/38; C01B 3/34; C01B 3/22
USPC ..................... 123/440; 60/605, 278; 436/141
See application file for complete search history.

(56) References Cited

U.S. PATENT DOCUMENTS

| | | | |
|---|---|---|---|
| 4,870,025 A | 9/1989 | Hurley et al. | |
| 5,070,024 A | 12/1991 | Bruno | |
| 5,221,517 A | 6/1993 | Takeda | |
| 6,242,263 B1 | 6/2001 | Faber et al. | |
| 2002/0021984 A1 | 2/2002 | Kroneisen | |
| 2011/0098936 A1 | 4/2011 | Bats et al. | |
| 2013/0008162 A1* | 1/2013 | Ruona | F01N 3/023 60/605.1 |
| 2014/0069086 A1* | 3/2014 | LaPointe | F02M 27/02 60/278 |
| 2015/0153316 A1 | 6/2015 | Abdul-Khalek | |
| 2015/0241399 A1 | 8/2015 | Li et al. | |

* cited by examiner

SYSTEMS AND METHODS FOR DETERMINING THE COMPOSITION OF GASEOUS FUEL

CROSS-REFERENCE TO RELATED APPLICATIONS

The present application is a U.S. national stage application claiming the benefit of International Application No. PCT/US2015/045516, filed on Aug. 17, 2015, which claims the benefit of priority to U.S. Provisional Patent Application No. 62/039,563, filed Aug. 20, 2014, titled " SYSTEMS AND METHODS FOR DETERMINING THE COMPOSITION OF GASEOUS FUEL." Both applications are incorporated herein by reference in their entirety.

BACKGROUND

A "raw fuel" stream typically refers to fuel that is obtained from a well. Often, such fuels are also referred to as "raw well head gases." Raw well head gases can be used by spark ignited piston engines in order to power generators, pumps, compressors, etc., that are employed for a variety of applications. In order to tune and optimize engine performance, it is desirable to know the relative amounts of methane, non-methane hydrocarbons, and carbon dioxide in the raw well head gas supplying the engine. This is because engine performance is often limited by autoignition of a fuel charge, which causes the phenomenon referred to as "knock," An engine experiencing knock can quickly be destroyed or otherwise damaged. Methane is very resistant to knock. However, most non-methane hydrocarbons are less resistant to knock, and therefore they tend to reduce engine performance as compared to methane. Carbon dioxide is an inert gas and does not contribute to the energy of the fuel. Accordingly, when carbon dioxide is present in a fuel, more total fuel must flow to maintain a certain engine power. Thus, knowing the composition of the fuel enables adjustments to engine configurations and the relative amounts of fuel required, which can improve engine performance and avoid potentially damaging engine knock.

SUMMARY

Disclosed herein are methods, systems, and computer-readable mediums for determining the composition of gaseous fuel. One embodiment relates to a method. The method comprises: providing an initial gaseous fuel stream at a fuel mass flow rate, wherein the initial fuel stream comprises methane, non-methane hydrocarbons, and inert gases; mixing air into the initial fuel stream upstream of a first catalyst, wherein the air is at a first air mass flow rate; oxidizing, by the first catalyst, only the non-methane hydrocarbons of the initial fuel stream to produce a resultant fuel stream comprising methane and inert gases; mixing air into the resultant fuel stream downstream of the first catalyst and upstream of a second catalyst, wherein the air is at a second air mass flow rate; oxidizing, by the second catalyst, only the methane hydrocarbons of the resultant fuel stream to produce an output fuel stream; and determining, using one or more processors, a mole ratio of the methane of the initial fuel stream, a mole ratio of the non-methane hydrocarbons of the initial fuel stream, and a mole ratio of the inert gases of the initial fuel stream, wherein the determination is based on the fuel mass flow rate, the first air mass flow rate, and the second air mass flow rate.

Another embodiment relates to a device for determining a relative composition of gaseous fuel. The device comprises a pump configured to direct an initial gaseous fuel stream over a first catalyst at a fuel mass flow rate, wherein the initial fuel stream comprises methane, non-methane hydrocarbons, and inert gases. The device further comprises a first mass flow controller configured to provide air at a first air mass flow rate to mix into the initial fuel stream upstream of the first catalyst. The device further comprises the first catalyst, configured to oxidize only the non-methane hydrocarbons of the initial fuel stream to produce a resultant fuel stream comprising methane and inert gases. The device further comprises a second mass flow controller configured to provide air at a second air mass flow rate to mix into the resultant fuel stream downstream of the first catalyst and upstream of a second catalyst. The device further comprises the second catalyst, configured to oxidize only the methane hydrocarbons of the resultant fuel stream to produce an output fuel stream. The device further comprises one or more processors configured to determine a mole ratio of the methane of the initial fuel stream, a mole ratio of the non-methane hydrocarbons of the initial fuel stream, and a mole ratio of the inert gases of the initial fuel stream, wherein the determination is based on the fuel mass flow rate, the first air mass flow rate, and the second air mass flow rate.

Another embodiment relates to a system. The system comprises a fuel source configured to supply an initial gaseous fuel stream that is directed over a first catalyst at a fuel mass flow rate, wherein the initial fuel stream is a raw well head gas that comprises methane, non-methane hydrocarbons, and inert gases. The system further comprises a first mass flow controller configured to provide air at a first air mass flow rate to mix into the initial fuel stream upstream of the first catalyst. The system further comprises the first catalyst, configured to oxidize only the non-methane hydrocarbons of the initial fuel stream to produce a resultant fuel stream comprising methane and inert gases. The system further comprises a second mass flow controller configured to provide air at a second air mass flow rate to mix into the resultant fuel stream downstream of the first catalyst and upstream of a second catalyst. The system further comprises the second catalyst, configured to oxidize only the methane hydrocarbons of the resultant fuel stream to produce an output fuel stream. The system further comprises a master controller comprising one or more processors. The one or more processors are configured to: control the first mass flow controller to adjust the first air mass flow rate; control the second mass flow controller to adjust the second air mass flow rate; determine a mole ratio of the methane of the initial fuel stream, a mole ratio of the non-methane hydrocarbons of the initial fuel stream, and a mole ratio of the inert gases of the initial fuel stream, wherein the determination is based on the fuel mass flow rate, the first air mass flow rate, and the second air mass flow rate; and transmit the determined mole ratios to a controller of an engine configured to combust the raw well head gas.

Still another embodiment relates to a method. The method includes providing an initial gaseous fuel stream having a methane hydrocarbon, non-methane hydrocarbon, and an inert gas at a fuel mass flow rate; mixing air at a first air mass flow rate into the initial gaseous fuel stream upstream of a first catalyst; oxidizing, by the first catalyst, the non-methane hydrocarbon in the initial gaseous fuel stream to produce a resultant fuel stream comprising the methane hydrocarbon and the inert gas; mixing air at a second air mass flow rate into the resultant fuel stream downstream of the first catalyst and upstream of a second catalyst; oxidizing, by the second catalyst, the methane hydrocarbon in the resultant fuel stream to produce an output fuel stream; and determining a value indicative of the methane hydrocarbon in the initial gaseous fuel stream, a value indicative of the non-methane hydrocarbon in the initial gaseous fuel stream, and a value indicative of the inert gas in the initial gaseous fuel stream. The determination is based on the fuel mass flow rate, the first air mass flow rate, and the second air mass flow rate.

Yet another embodiment relates to a system. The system includes a pump, a first mass flow device, a second mass flow device, a first catalyst, a second catalyst, and a controller. The pump is structured to direct a gaseous fuel stream over a first catalyst at a fuel mass flow rate. The gaseous fuel stream includes a methane hydrocarbon, non-methane hydrocarbon, and an inert gas. The first mass flow control device is structured to provide air at a first air mass flow rate to mix into the gaseous fuel stream upstream of the first catalyst. The first catalyst positioned to oxidize the non-methane hydrocarbon in the gaseous fuel stream to produce a resultant fuel stream comprising the methane hydrocarbon and the inert gas. The second mass flow control device structured to provide air at a second air mass flow rate to mix into the resultant fuel stream downstream of the first catalyst and upstream of a second catalyst. The second catalyst is positioned to oxidize the methane hydrocarbon in the resultant fuel stream to produce an output fuel stream. The controller is structured to determine a composition of the gaseous fuel stream based on the fuel mass flow rate, the first air mass flow rate, and the second air mass flow rate. Determining the composition of the gaseous fuel stream includes determining a value indicative of the methane hydrocarbon in the gaseous fuel stream; determining a value indicative of the non-methane hydrocarbon in the gaseous fuel stream; and determining a value indicative of the inert gas in the gaseous fuel stream.

Another embodiment relates to an apparatus. The apparatus includes a first mass flow controller, a second mass flow controller, and a master controller. The first flow controller is structured to provide air at a first air mass flow rate to mix into a fuel stream upstream of a first catalyst. The fuel stream is directed over the first catalyst at a fuel mass flow rate. The fuel stream includes a methane hydrocarbon, a non-methane hydrocarbon, and an inert gas. The a second mass flow controller is structured to provide air at a second air mass flow rate to mix into the fuel stream downstream of the first catalyst and upstream of a second catalyst. The master controller is communicably and operatively coupled to each of the first mass flow controller and the second mass flow controller. The master controller is structured to determine a composition of the fuel stream including a value indicative of the methane hydrocarbon in the fuel stream, a value indicative of the non-methane hydrocarbon in the fuel stream, and a value indicative of the inert gas in the fuel stream. The determination is based on the fuel mass flow rate, the first air mass flow rate, and the second air mass flow rate. In one embodiment, the apparatus further includes an engine controller. The engine controller is structured to control operation of an engine based on the composition of the fuel stream. The engine is structured to combust a second fuel stream associated with the first fuel stream.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAW

The foregoing and other features of the present disclosure will become more fully apparent from the following description and appended claims, taken in conjunction with the accompanying drawings. Understanding that these drawings depict only several implementations in accordance with the disclosure and are, therefore, not to be considered limiting of its scope, the disclosure will be described with additional specificity and detail through use of the accompanying drawings.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

Described herein are techniques for determining the composition of gaseous fuel. According to the disclosure herein the relative amounts of methane, non-methane hydrocarbons, and inert gases in a raw fuel stream can be determined. Although the term "raw fuel" and "raw well head gas" in this context often refers to fuels that are obtained from wells, the present disclosure is not limited to such supplied fuels. The techniques disclosed herein may be utilized to assess any gaseous fuel supply. For the purposes of this disclosure, references to "inert gases" will be assumed to be carbon dioxide (CO2), which is an adequate surrogate, although other surrogate gas mixtures may be used. Accordingly, these raw well head fuels can be characterized by the chemical formula: $(CH4_x)(CnH\mu_y)(CO2_z)$. Here, x represents the number of moles of methane per mole of fuel, y represents the number of non-methane hydrocarbons per mole of fuel, and z represents the number of moles of inert gases per mole of fuel (with carbon dioxide being chosen as a representative "inert" gas). The non-methane hydrocarbons may be assumed to be represented by a single species of hydrocarbons having n moles of carbon per mole of non-methane hydrocarbon, and µ can represent the number of moles of hydrogen per mole of non-methane hydrocarbon. In general, a majority of raw well head gases can be represented by choosing n=3 and μ=8 (i.e., propane), although the present disclosure is not limited to such a configuration.

The disclosure herein also provides systems and devices that can monitor the relative amounts of methane, non-methane hydrocarbons, and carbon dioxide of the fuel stream entering an engine. Only a very small amount of the fuel stream entering the engine must pass through the systems or devices. In one embodiment, only approximately 0.25 lb./hr. of raw fuel must be processed by the systems or devices to perform their functions. This low rate of fuel is "sacrificial" and will not be used by the engine. Other fuel amounts may also be used. Once the relative proportions of methane, non-methane hydrocarbons, and carbon dioxide in the raw fuel are known (e.g., x, y, and z), parameters that characterize engine performance can be computed. Such parameters typically include the methane number, the lower heating value, the volumetric heating value, and Wobbe index, among others. For example, a target ratio of fuel-to-air and spark timing for optimal performance and emissions compliance can be determined for a given engine by knowing the methane number and lower heating value of the fuel.

In general, when a raw fuel stream is directed over a typical oxidation catalyst, methane in the fuel will pass through without being oxidized. A specially designed catalyst is required to oxidize methane. Additionally, carbon dioxide in the original raw fuel stream will pass through both types of catalysts without being affected. However, if an appropriate amount of air is mixed with the raw fuel stream upstream of the typical oxidation catalyst, all non-methane hydrocarbons from the original raw fuel stream can be oxidized, but the methane and carbon dioxide present in the original raw fuel stream will pass through unchanged. Then, if more air is added to the gases downstream of the typical catalyst and upstream of the special catalyst, and if the amount of the air is adjusted appropriately, the methane can be fully oxidized by the special catalyst. The carbon dioxide in the original raw fuel stream may again pass through the special catalyst unchanged.

According to the disclosure herein, the mass flow of the original raw fuel stream entering a device as disclosed herein, the mass flow of the air entering upstream of the typical catalyst, and the mass flow of the air upstream of the special catalyst may be known or determined, and the exact proportions of the methane, non-methane hydrocarbons, and the carbon dioxide in the original raw fuel stream can be precisely determined. Various flow controllers may be used, as will be described, to allow a "correct" amount of air to be admitted to the streams entering both catalysts. Combustion with the chemically correct amount of air is known as "stoichiometric" combustion, which implies that the fuel and air mixture has neither too much nor too little air, but just enough to fully oxidize the fuel into water and carbon dioxide. Throughout the disclosure herein, a typical oxidation catalyst may be referred to as a Non-methane Hydrocarbon Catalyst, or a NMHC Catalyst. A special catalyst that can oxidize urethane may be referred to as a Methane Oxidation Catalyst.

Figure 1:
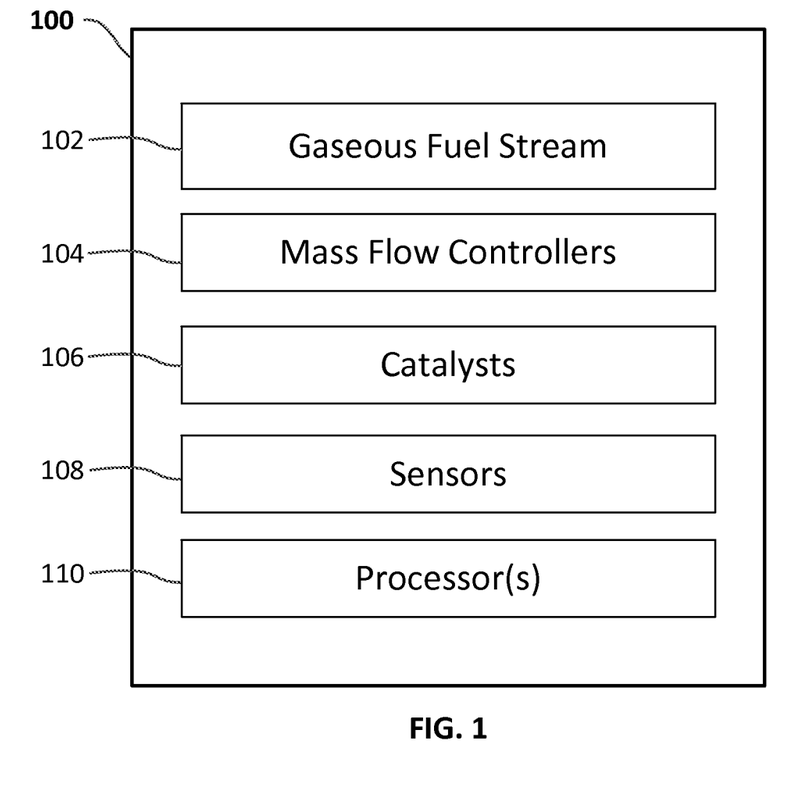
FIG. 1 is a block diagram of a system for determining the composition of gaseous fuel, according to one embodiment.

Referring to FIG. 1, a block diagram of a general system 100 for determining the composition of gaseous fuel is shown, according to one embodiment. System 100 operates over a gaseous fuel stream 102 as the source fuel. In one embodiment, fuel stream 102 comprises a raw well gas that may be supplied to one or more engines. One or more mass flow controllers 104 may be used to control the flow of the fuel and added air through system 100. A flow rate may be held constant or adjusted. In one embodiment, the flow rate of fuel stream 102 is at a rate necessary to maintain a stoichiometric combustion of the non-methane hydrocarbons and the methane of the initial fuel stream by catalysts 106. The rate may further be such that a chemically correct stoichiometric fuel to air ratio is maintained. Multiple catalysts 106 may be used to oxidize the non-methane hydrocarbons of fuel stream 102, and also to oxidize the methane of fuel stream 102. In one embodiment, a first catalyst is used to oxidize the non-methane hydrocarbons and a second catalyst is used to oxidize the methane of fuel stream 102. One or more sensors 108 (e.g., oxygen sensors) may be used to determine the amount of oxygen in fuel stream 102 as it flows through system 100 and is oxidized by catalysts 106. In one embodiment, sensors 108 include zirconia based oxygen sensors. One or more processors 110 may be used to control the flow process of fuel stream 102 and air throughout the system 100. For example, processors 110 may monitor, record (in Memory), and analyze values provided by sensors 108, and determined flow rates based on such values. The processors 110 may generate the signals necessary to control mass flow controllers 104 or communicate with any other components of system 100. Additionally, processors 110 may determine the composition of fuel steam 102 and generate reporting data and transmit data (via a transmitter or other communication connection) to external systems.

Figure 2:
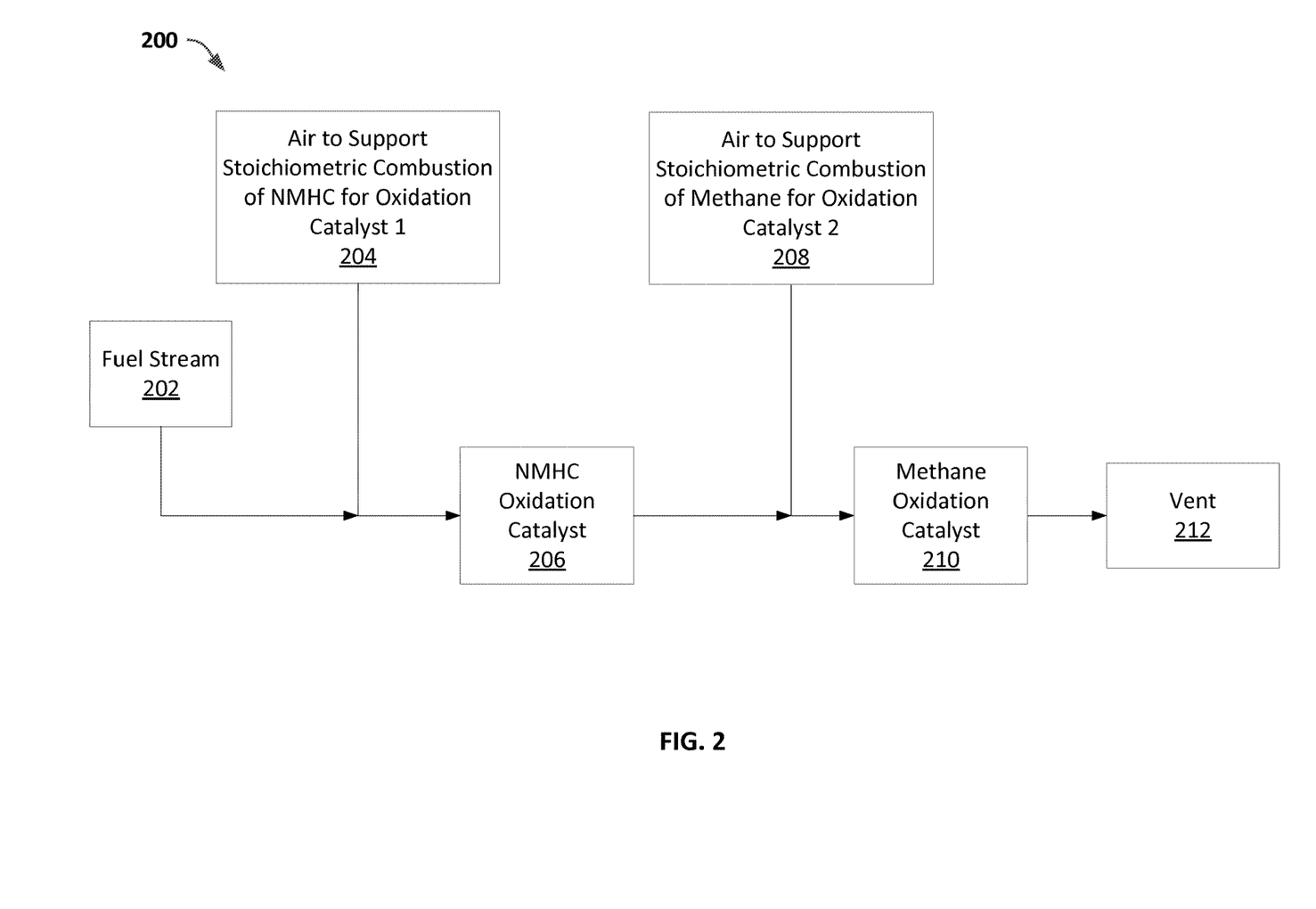
FIG. 2 is a diagram of a system for determining the composition of gaseous fuel, according to one embodiment.

Referring to FIG. 2, a diagram of a system 200 for determining the composition of gaseous fuel is shown, according to one embodiment. System 200 includes an initial raw fuel stream 202. In one embodiment, fuel stream 202 is a gaseous fuel supplied by a well (which may ultimately be used by an engine). For example, a small amount of fuel from source fuel stream 202 is admitted to system 200. Air may then be admitted 204 to fuel stream 202, where is can be mixed prior to being introduced into the NMHC Oxidation Catalyst 206. For example, a mass flow controller may be electronically controlled in order to adjust the rate of air admitted. Multiple components (e.g., pressure regulators, filters, etc.) may also be used in such a process of controlling the air flow. In one embodiment, the amount of air admitted at this point is the amount required to support stoichiometric combustion of the non-methane hydrocarbons present in the original raw fuel stream 202. Downstream of the NMHC Oxidation Catalyst 206, air may be admitted 208 to the stream of gases flowing out of NMHC Oxidation Catalyst 206 and mixed. For example, another mass flow controller may be electronically controlled in order to adjust the rate of air admitted. In one embodiment, a single mass flow controller may be used to admit air, with multiple routings of the admitted air. Such an embodiment may include the necessary conduit, valves, etc., required to admit air to be mixed and properly route the admitted air. In one embodiment, the amount of air admitted at this point is the amount required to support stoichiometric combustion of the methane present in the original fuel stream 202 by Methane Oxidation Catalyst 210. After flowing through both NMHC Oxidation Catalyst 206 and Methane Oxidation Catalyst 210, the gases flowing from Methane Oxidation Catalyst 210 may be exhausted via vent 212.

As NMHC Oxidation Catalyst 206 sloes not oxidize methane, the amount of air admitted upstream of it (i.e., at 204) can be controlled to be the stoichiometric quantity needed to fully oxidize only the non-methane hydrocarbons of the original raw fuel stream 202. Additionally, the amount of air entering the stream of gases downstream of NMHC Oxidation Catalyst 206 (i.e., at 208) can be controlled to be the stoichiometric amount required to fully oxidize all methane from the original raw fuel stream 202 by Methane Oxidation Catalyst 210. In one embodiment, system 200 can require a determination of the mass flow rates of fuel and of air in order to provide stoichiometric combustion of the non-methane hydrocarbons by NMHC Oxidation Catalyst 206. Additionally, the mass flow rate of air to provide stoichiometric combustion of the methane in Methane Oxidation Catalyst 210 may also be determined. In general, the amount of fuel entering system 200 is low (e.g., on the order of 0.25 lb./hr., etc.), although this amount may vary.

Figure 3:
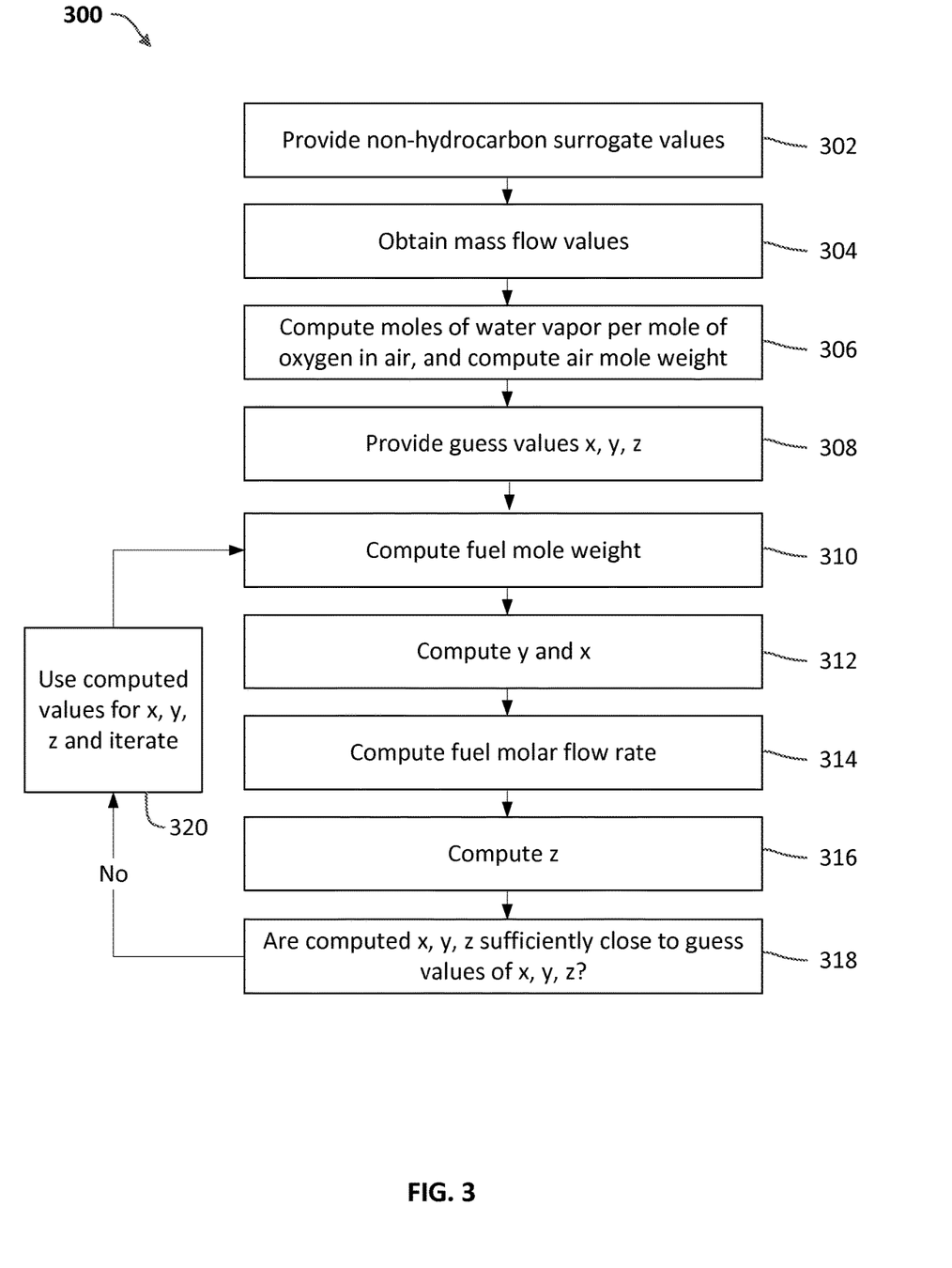
FIG. 3 is a flow diagram of a process for determining the composition of gaseous fuel, according to one embodiment.

A determination of the moles of methane per mole of fuel (x), the moles of non-methane hydrocarbons per mole of fuel (y), and the moles of carbon dioxide per mole of fuel (z), can be determined via process 300 described in FIG. 3. In some embodiments, it may be necessary to estimate the number of moles of carbon per mole of non-methane hydrocarbons (n), and number of moles of hydrogen per mole of non-methane hydrocarbons (μ). However, in some embodiments it is assumed that n=3 and μ=8, which represents propane, without sacrificing significant accuracy. Other values for n and μ may also be used if desired. In some embodiments, increased accuracy can be obtained if the relative humidity fraction (rh) of the combustion air admitted to system 200 is known or determined, in general, valid values for rh are typically between 0 and 1.

Referring to FIG. 3, a flow diagram of a process 300 for determining the composition of gaseous fuel is shown, according to an embodiment. In alternative embodiments, fewer, additional, and/or different steps may be performed. Also, the use of a flow diagram is not meant to be limiting with respect to the order of steps performed. Various functions may be utilized to compute the following values discussed throughout process 300. Such functions are provided below, however, the present disclosure is not limited to use of the provided functions and other computations may be performed in order to obtain the discussed values. Process 300 includes providing non-hydrocarbon surrogate values 302. In one embodiment, the surrogate values are chosen to be representative of propane (e.g., n=3 and μ=8). The mass flow rates may then be obtained (304). For example, a mass flow meter, a critical flow orifice configured to restrict flow of a fluid therethrough, or another flow rate control device may be used to control and determine the mass flow rate. The moles of water vapor per mole of oxygen in air may then be computed (306). Additionally, the air mole weight may also be computed (306). Guess/estimate values for x, y, and z (i.e., estimates for the number of moles of methane per mole of fuel, the number of non-methane hydrocarbons per mole of fuel, and the number of moles of inert gases per mole of fuel) may be provided (308). In one embodiment, the initial guess values may be based on a prior knowledge of reasonable values for x, y, and z corresponding to a particular configuration. The mole weight of the gaseous fuel may then be computed (310). Based on the above determined values, computed values of y (the number of non-methane hydrocarbons per mole of fuel) and x (the number of moles of methane per mole of fuel) can be determined (312). The fuel molar flow rate may then be computed (314). A computed value of z (the number of moles of inert gases per mole of fuel) may then be determined (316). For example, z may be computed by finding the root of the function, zFunc(z), provided below. The computed values of x, y, and z may then be compared to the estimate values of x, y, and z (318). If the estimate values are sufficiently close to the computed values, process 300 may terminate. However, if the estimate values are not sufficiently close to the computed values, process 300 may iterate and the computed values for x, y, and z may be used during the next iteration (320).

After x, y, and z are computed (e.g., via process 300), critical parameters of the original fuel stream can be determined. For example, the methane number, lower heating value, volumetric heating value, and Wobbe index may be determined. The values may be provided to an engine controller or other external system (e.g., an operator's computing system). By providing one or more of these parameters, an engine can be set for optimal ratios of fuel-to-air flow as well as spark timing in order to best accommodate the characteristics of the raw fuel stream.

Figure 5:
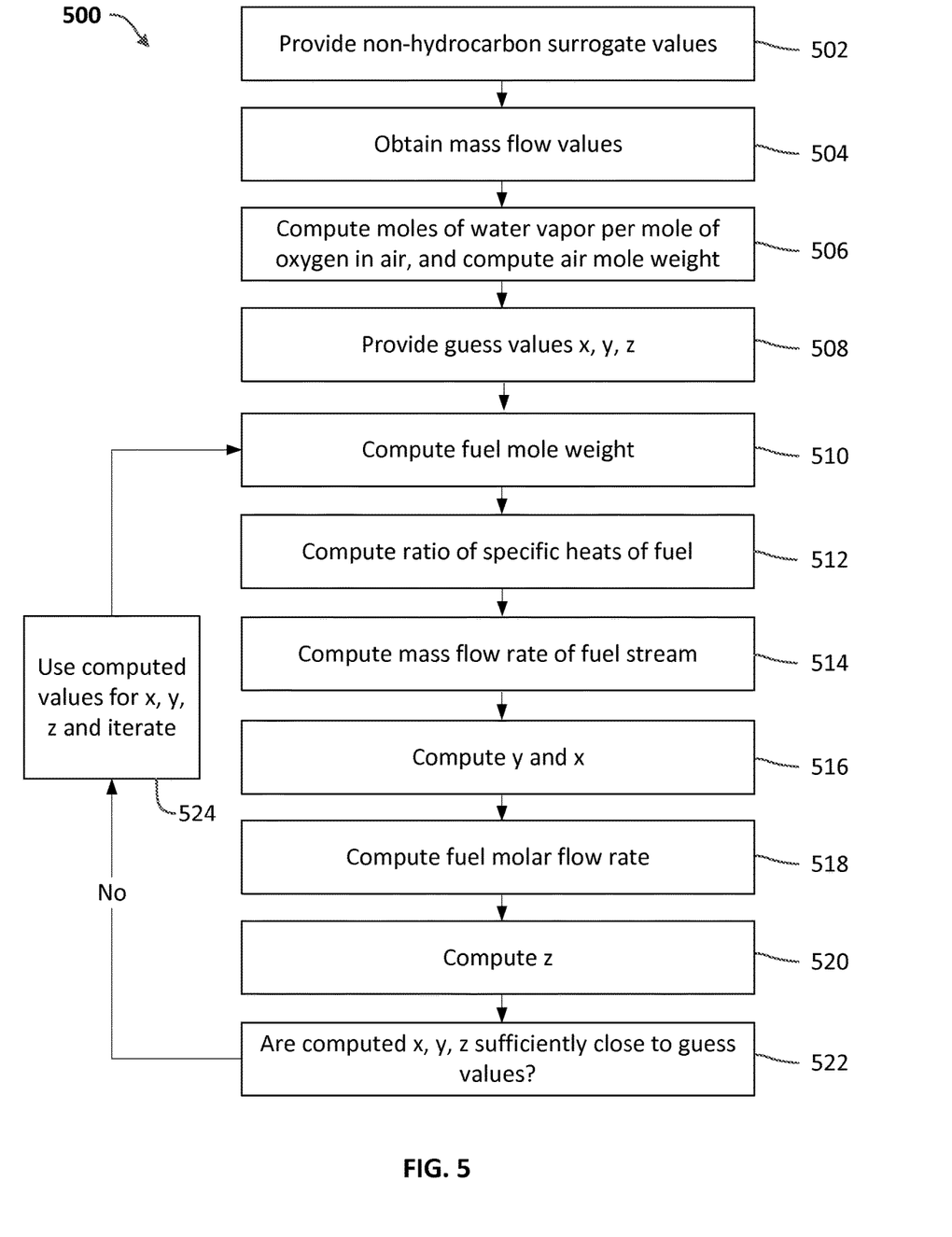
FIG. 5 is a flow diagram of a process for determining the composition of gaseous fuel, according to one embodiment.

Functions that may be utilized in the computation of process 300 (and process 500 of FIG. 5) are provided below:

$$wtrFunc(rh) = (-8.279417 \cdot 10^{-4}) + (1.600004 \cdot 10^{-1}) \cdot rh$$

$$M_{Air} = (M_{O2} + AirN2 \cdot M_{N2} + AirCO2 \cdot M_{CO2} + wrt \cdot M_{H2O})$$

$$Mn_F = \frac{x \cdot M_{CH4} + y \cdot (n \cdot M_C + \mu \cdot M_H) + z \cdot M_{CO2}}{x + y + z}$$

$$M_F = (x \cdot M_{CH4} + y \cdot (n \cdot M_C + \mu \cdot M_H) + z \cdot M_{CO2}$$

$$k = kFunc(x, y, z, T_F)$$

$$mdot_F = C \cdot A \cdot P_F \cdot \sqrt{k \cdot \left(\frac{Mn_F}{T_F \cdot UPGC}\right) \cdot \left(\frac{2}{k+1}\right)^{\left(\frac{k+1}{k-1}\right)}}$$

$$y = \frac{4 \cdot M_F \cdot mdot_{Air1}}{M_{Air} \cdot \mu \cdot mdot_{Fuel} + 4 \cdot M_{Air} \cdot mdot_{Fuel} \cdot n}$$

$$x = \frac{M_F \cdot mdot_{Air2}}{2 \cdot M_{Air} \cdot mdot_{Fuel}}$$

$$F1 = \frac{mdot_{Fuel}}{M_F}$$

$$z = root(zFunc(z), z)$$

The zFunc(z) computation is described below:

$$zFunc(z) := jnk1 \leftarrow F1 \cdot \left[M_F + \left[y \cdot \left(n + \frac{\mu}{4}\right) + 2 \cdot x\right] \cdot M_{Air}\right]$$

$$zFunc(z) :=$$

$$jnk2 \leftarrow \left[F1 \cdot \left[y \cdot \left(n + \frac{\mu}{4}\right) \cdot AirCO2 + y \cdot n + z\right] + 2 \cdot (F1 \cdot x) \cdot \left(\frac{1}{2} + AirCO2\right)\right] \cdot$$

$$M_{CO2} + \left[F1 \cdot \left[\frac{y \cdot \mu}{2} + y \cdot \left(n + \frac{\mu}{4}\right) \cdot wtr\right] + 2 \cdot (F1 \cdot x) \cdot (1 + wtr)\right] \cdot$$

$$M_{H2O}$$

$$zFunc(z) := jnk3 \leftarrow \left[F1 \cdot \left[y \cdot \left(n + \frac{\mu}{4}\right) \cdot AirN2\right] + 2 \cdot (F1 \cdot x) \cdot AirN2\right] \cdot M_{N2}$$

$$zFunc(z) := out \leftarrow jnk1 - (jnk2 + nk3)$$

$$zFunc(z) := out$$

Definitions of variables that are used in implementing the above functions are provided in Table 1. These parameters may be used in determining the composition of a gaseous fuel stream as described herein (e.g., in processes 300 and 500, etc.).

TABLE 1

| Parameter | Description |
| --- | --- |
| n | Carbon number of non-methane hydrocarbons in fuel stream |

TABLE 1-continued

| Parameter | Description |
|---|---|
| $\mu$ | Hydrogen number of non-methane hydrocarbons in fuel stream |
| $mdot_F$ | Mass flow rate of fuel stream |
| $mdot_{Air-1}$ | Mass air flow rate entering NMHC Oxidation Catalyst |
| $mdot_{Air-2}$ | Mass air flow rate entering Methane Oxidation Catalyst |
| AirtN2 | Moles of nitrogen per mole of oxygen in air |
| AirCO2 | Moles of carbon dioxide per mole of oxygen in air |
| rh | Relative humidity fraction |
| $M_{Air}$ | Molal weight of air |
| $M_{O2}$ | Molecular weight of oxygen |
| $M_{N2}$ | Molecular weight of nitrogen |
| $M_{CO2}$ | Molecular weight of carbon dioxide |
| $M_{H2O}$ | Molecular weight of water vapor |
| $Mn_F$ | Molecular weight of fuel |
| $M_F$ | Molal weight of fuel |
| x | Moles of methane per mole of fuel |
| y | Moles of non-methane hydrocarbons per mole of fuel |
| z | Moles of inert gases (e.g., carbon dioxide) per mole of fuel |
| k | Ratio of specific heats of fuel |
| $T_F$ | Temperature of fuel |
| $P_F$ | Pressure upstream of fuel critical flow orifice |
| kFunc(x, y, z, $T_F$) | Function to compute ratio of specific heats of fuel |
| zFunc(z) | Function to compute z of fuel |

Figure 4:
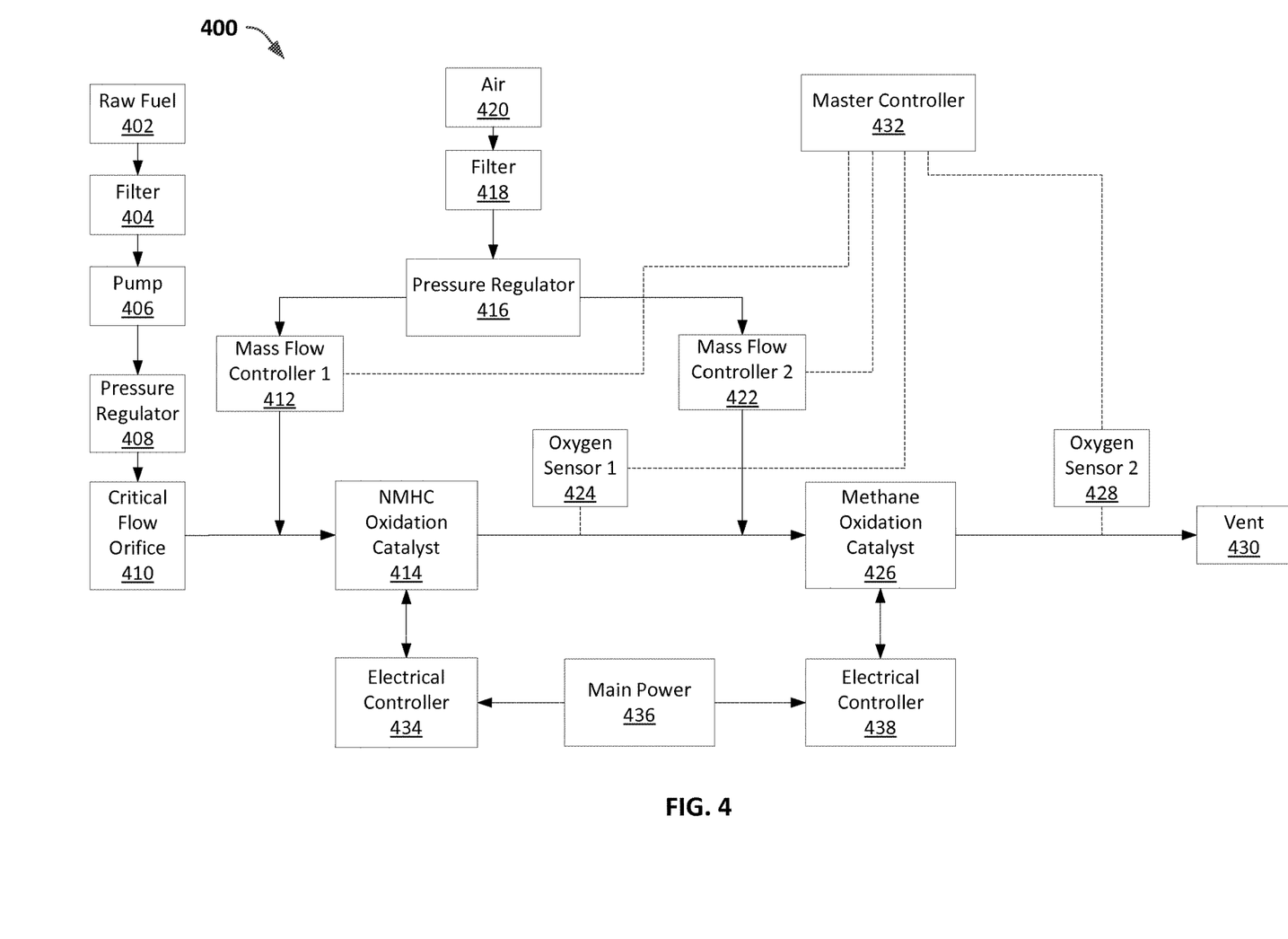
FIG. 4 is a diagram of a system for determining the composition of gaseous fuel, according to one embodiment.

Referring to FIG. 4, a diagram of a system 400 for determining the composition of gaseous fuel is shown, according to one embodiment. In this embodiment, the mass flow rate of the raw fuel stream 402 can be determined using critical flow orifice 410. Raw fuel stream 402 may be initially filtered (via filter 404). Any filter may be utilized to clean fuel stream 402 prior to being processed. After being filtered, pump 406 and pressure regulator 408, which are positioned upstream of the critical flow orifice 410 can be used to maintain a certain pressure ratio across the critical flow orifice 410 to ensure the flow is restricted to a particular flow rate.

The amount of air needed to oxidize the non-methane hydrocarbons in the original fuel stream 402, with NMHC Oxidation Catalyst 414 maintained at the correct stoichiometric fuel and air ratio, may be controlled by a first mass flow controller 412. Mass flow controller 412 receives appropriate control signals from a master controller 432. In order to generate the appropriate control signals, master controller 432 can monitor the level of oxygen present in the gases downstream of the NMHC Oxidation Catalyst 414. To do so, a first oxygen sensor 424 may provide feedback related to the product of oxidation by NMHC Oxidation Catalyst 414. In one embodiment, NMHC Oxidation Catalyst 414 is designed to enable methane from the original raw fuel stream 402 to pass through without change, along with the carbon dioxide from original raw fuel stream 402. Based on the products, master controller 432 can correctly control mass flow controller 412 and can adjust the amount of air introduced (and in turn adjust the oxidation of non-methane hydrocarbons by NMHC Oxidation Catalyst 414). In one embodiment, oxygen sensor 424 includes a "switching" zirconia based oxygen sensor (e.g., similar to that typically used in automotive applications). However, other types of oxygen sensors may be utilized. In one embodiment, master controller 432 manages mass flow controller 412 by "dithering" the rate of air flow, first slightly below or above, then slightly above or below, the rate of air flow necessary to maintain stoichiometric combustion of the non-methane hydrocarbons within NMHC Oxidation Catalyst 414. The "dithering" amount can be indicated by oxygen sensor 424 as it changes state (e.g., from 0 to 1, etc.) when oxygen appears in the stream at its location (i.e., when slightly too much air 420 is admitted) and then when oxygen disappears (i.e., when slightly too little air 420 is admitted). Accordingly, master controller 432 may control a mass flow controller in response to data provided by an oxygen sensor.

The amount of air necessary to oxidize the methane from the original raw fuel stream 402 with Methane Oxidation Catalyst 426 at the correct stoichiometric fuel and air ratio can be controlled with a second mass flow controller 422. In one embodiment, mass flow controller 422 receives appropriate control signals from master controller 432. Master controller 432 may monitor signals from a second oxygen sensor 428 in order to correctly control mass flow controller 422. In one embodiment, oxygen sensor 428 includes a "switching" zirconia based oxygen sensor (e.g., similar to as described for oxygen sensor 424). Master controller 432 manages mass flow controller 422 by "dithering" the rate of air flow, first slightly below or above, then slightly above or below, the rate of air flow necessary to maintain stoichiometric combustion of the methane within Methane Oxidation Catalyst 426. The "dithering" amount can be indicated by oxygen sensor 428 as it changes state (e.g., from 0 to 1, etc.) when oxygen appears in the stream at its location (i.e., when slightly too much air 420 is admitted) and then when oxygen disappears (i.e., when slightly too little air 420 is admitted), and master controller 432 may interpret the data from oxygen sensor 428 in order to determine an amount of adjustment to be made to mass flow controller 422. The fuel stream 402 passes through Methane Oxidation Catalyst 426, and the remaining fuel stream 402 may be vented via a vent 430. In general, the air 420 discussed herein may be supplied from any air source, and may be filtered (e.g., via an air filter 418, etc.) prior to being admitted to fuel stream 402. A pressure regulator 416 and/or manifold may also be used to maintain a proper pressure and flow rate of air 420 to mass flow controllers 412 and 422.

Typically, non-methane hydrocarbon catalysts can function properly when the temperature of the catalyst is maintained at a temperature (generally a constant temperature) within a range of 250° C. to 350° C. A first electrical controller 434 may be employed to maintain NMHC Oxidation Catalyst 414 at a particular temperature (e.g., within the 250° C. to 350° C. range) by way of resistive heater elements encasing or coupled to the catalyst. Other heating mechanisms may also be used and controlled by electrical controller 434. Catalysts capable of oxidizing methane need to be maintained at a higher temperature, typically within the range of 550° C. to 650° C. Accordingly, a second electrical controller 438 may be used to maintain Methane Oxidation Catalyst 426 a particular temperature (e.g., within the 550° C. to 650° C. range) by way of resistance heater elements encasing or coupled to the catalyst. A min power source 436 may be used to supply power to the electrical controllers (and to any of the other controllers discussed herein. In one embodiment, electrical controller 434 and electrical controller 438 are part of an electrical controller unit that is capable of managing the temperatures of both NMHC Oxidation Catalyst 414 and Methane Oxidation Catalyst 426. Master controller 432 may also interface with and control the electrical controllers.

Referring to FIG. 5, a flow diagram of a process 500 for determining the composition of gaseous fuel is shown, according to an embodiment. In alternative embodiments, fewer, additional, and/or different steps may be performed. Also, the use of a flow diagram is not meant to be limiting with respect to the order of steps performed. Process 500 may be used to determine x, y, and z of a raw fuel stream supplied to a system as described with respect to FIG. 4. Various functions may be utilized to compute the following values discussed throughout process 500. Such functions are provided above, however, the present disclosure is not limited to use of the provided functions and other computations may be performed to obtain the discussed values. Process 500 includes providing non-hydrocarbon surrogate values 502. In one embodiment, the surrogate values are chosen to be representative of propane (e.g., n=3 and μ=8). The mass flow rates may then be obtained (504). For example, a mass flow meter, a critical flow orifice (e.g., critical flow orifice 410) configured to restrict flow of a fluid therethrough, or another flow rate detection device may be used to determine the mass flow rate. The moles of water vapor per mole of oxygen in air may then be computed (506). Additionally, the air mole weight may also be computed (506). Guess/estimate values for x, y, and estimates for the number of moles of methane per mole of fuel, the number of non-methane hydrocarbons per mole of fuel, and the number of moles of inert gases per mole of fuel) may be provided (508). The mole weight of the gaseous fuel may then be computed (510). The ratio of specific heats of fuel may also be computed (512). The mass flow rate of the fuel stream may also be computed (514). Based on the above determined values, computed values of y (the number of non-methane hydrocarbons per mole of fuel) and x (the number of moles of methane per mole of fuel) can be determined (516). The fuel molar flow rate may then be computed (518). A value of z (the number of moles of inert gases per mole of fuel) may then be computed (520). For example, z may be computed by finding the root of the function, zFunc(z), provided above. The computed values of x, y, and z may then be compared to the estimate values of x, y, and z (522). If the estimate values are sufficiently close to the computed values, process 500 may terminate. However, if the estimate values are not sufficiently close to the computed values, process 500 may iterate and the computed values for x, y, and z may be used during the next iteration (524). Upon the conclusion of the iteration of steps 510-524, critical parameters of the original fuel stream can be determined. For example, the methane number, lower heating value, volumetric heating value, and Wobbe index may be determined Other parameters may also be determined.

Figure 6:
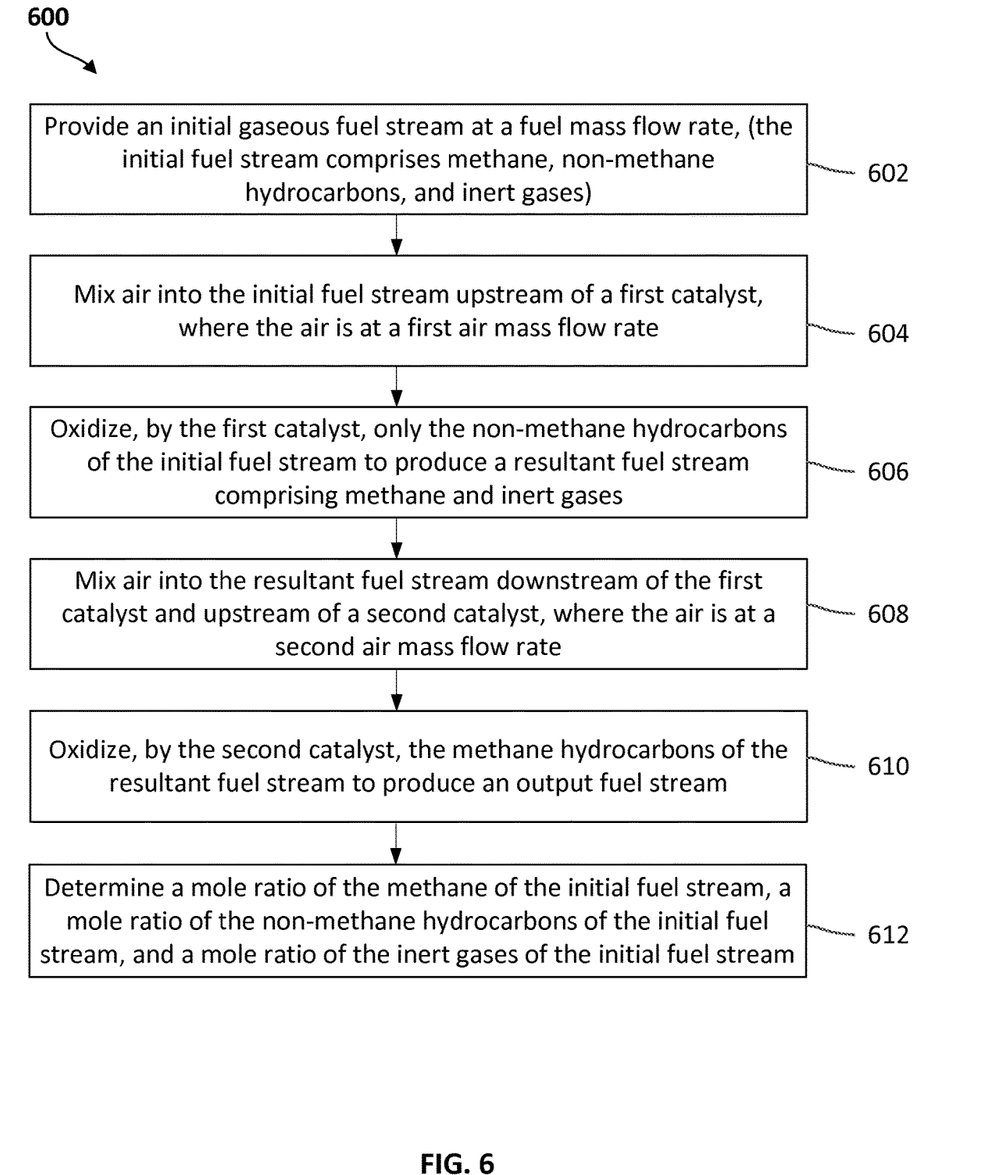
FIG. 6 is a flow diagram of a general process for determining the composition of gaseous fuel, according to one embodiment.

Referring to FIG. 6, a flow diagram of a general process 600 for determining the composition of gaseous fuel is shown, according to an embodiment. In alternative embodiments, fewer, additional, and/or different steps may be performed. Also, the use of a flow diagram is not meant to be limiting with respect to the order of steps performed. An initial gaseous fuel stream is provided at a fuel mass flow rate (602). The initial fuel stream comprises methane, non-methane hydrocarbons, and inert gases. In one embodiment, the fuel stream is supplied from a well. Air is mixed into the initial fuel stream upstream of a first catalyst, where the air is at a first air mass flow rate (604). The first catalyst then oxidizes only the non-methane hydrocarbons of the initial fuel stream to produce a resultant fuel stream comprising methane and inert gases (606). Air is mixed into the resultant fuel stream downstream of the first catalyst and upstream of a second catalyst, where the air is at a second air mass flow rate (608). The second catalyst oxidizes only the methane hydrocarbons of the resultant fuel stream to produce an output fuel stream (610). A mole ratio of the methane of the initial fuel stream, a mole ratio of the non-methane hydrocarbons of the initial fuel stream, and a mole ratio of the inert gases of the initial fuel stream may then be each determined (612). For example, measurements may be taken (e.g., using oxygen sensors, flow rate sensors, etc.) as the fuel stream flows and is oxidized as discussed above. Based on such measurements, the mole ratios related to the composition of the gaseous fuel can be determined.

Figure 7:
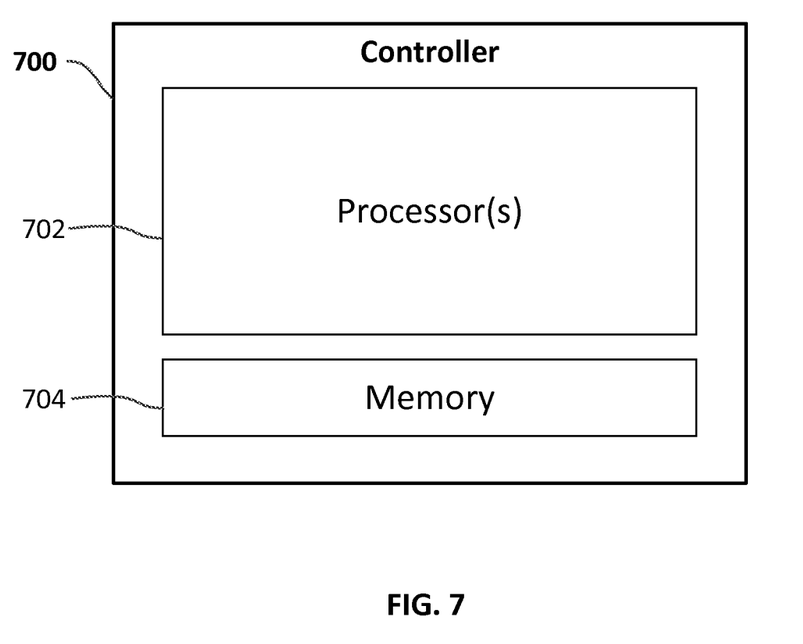
FIG. 7 is a block diagram of a controller for implementing the techniques disclose herein, according to one embodiment.

In any of the embodiments discussed herein, the controllers may form a portion of a processing subsystem including one or more computing devices having memory, processing, and communication hardware. The controllers may be a single device or a distributed device, and the functions of the controllers may be performed by hardware and/or as computer instructions on a non-transient computer readable storage medium, and functions may be distributed across various hardware or computer based components. Referring to FIG. 7, a controller 700 is shown, which may be any of the controllers discussed herein. Controller 700 may also be used to implement the techniques and methods discussed herein. For example, controller 700 may be master controller 432 of FIG. 4. In addition, controller 700 may be configured to perform the computations discussed herein (e.g., the computations of processes 300 and 500, etc.) and generate the signals necessary to interface with other devices in order to determine composition of gaseous fuel. In certain embodiments, controller 700 is part of a sensor device configured to determine the composition of gaseous fuel. Such a device may include components as discussed herein (e.g., the components of systems 100, 200, or 400, etc.). In certain embodiments, controller 700 is part of a single controller device that includes mass flow controllers and/or oxygen sensors.

Certain operations of controller 700 (or master controller 432) described herein include operations to interpret and/or to determine one or more parameters. Interpreting or determining, as utilized herein, includes receiving values by any method known in the art, including at least receiving values from a datalink or network communication, receiving an electronic signal (e.g. a voltage, frequency, current, or PWM signal) indicative of the value, receiving a computer generated parameter indicative of the value, reading the value from a memory location on a non-transient computer readable storage medium, receiving the value as a run-time parameter by any means known in the art, and/or by receiving a value by which the interpreted parameter can be calculated, and/or by referencing a default value that is interpreted to be the parameter value.

As shown FIG. 7, controller 700 includes a processing circuit having a processor 702 and a memory 704. Processor 702 may be implemented as a general-purpose processor, an application specific integrated circuit (ASIC), one or more field programmable gate arrays (FPGAs), a digital signal processor (DSP), a group of processing components, or other suitable electronic processing components. One or more memory devices 704 (e.g., NVRAM, RAM, ROM, Flash Memory, hard disk storage, etc.) may store data and/or computer code for facilitating the various processes described herein. Thus, one or more memory devices 704 may be communicably connected to processor 702 and provide computer code or instructions to processor 702 for executing the processes described in regard to controller 700 herein. Moreover, one or more memory devices 704 may be or include tangible, non-transient volatile memory or non-volatile memory. Accordingly, the one or more memory devices 704 may include database components, object code components, script components, or any other type of information structure for supporting the various activities and information structures described herein.

In addition, memory 704 may include memory storage physically located elsewhere, e.g., any cache memory in the processor 702 as well as any storage capacity used as a virtual memory, e.g., as stored on a mass storage device, etc. Controller 700 may also include any additional networking components or transmitters necessary to communicate with external configuration/control systems (e.g., Wi-Fi networking components, radiofrequency components, COM ports, sensor relays/connections, etc.). For example, determined composition of a gaseous fuel may be transmitted to an engine control unit or other computing system.

Memory 704 may further include various modules for completing the activities described herein. More particularly, memory 704 may include various modules to determine a composition of a gaseous fuel. While various modules with particular functionality may be included in memory 704, it should be understood that controller 700 and memory 704 may include any number of modules for completing the functions described herein. For example, the activities of multiple modules may be combined as a single module, additional modules with additional functionality may be included, etc. Further, it should be understood that controller 700 may further control other activity beyond the scope of the present disclosure Example and non-limiting module implementation elements include sensors providing any value determined herein, sensors providing any value that is a precursor to a value determined herein, datalink and/or network hardware including communication chips, oscillating crystals, communication links, cables, twisted pair wiring, coaxial wiring, shielded wiring, transmitters, receivers, and/or transceivers, logic circuits, hard-wired logic circuits, reconfigurable logic circuits in a particular non-transient state configured according to the module specification, any actuator including at least an electrical, hydraulic, or pneumatic actuator, a solenoid, an op-amp, analog control elements (springs, filters, integrators, adders, dividers, gain elements), and/or digital control elements.

Communication between and among controller 700 and the components of system 100, system 200, and/or system 400 may be via any number of wired or wireless connections. For example, a wired connection may include a serial cable, a fiber optic cable, a CAT5 cable, or any other form of wired connection. In comparison, a wireless connection may include the Internet, Wi-Fi, cellular, radio, etc. In one embodiment, a controller area network (CAN) bus provides the exchange of signals, information, and/or data. The CAN bus includes any number of wired and wireless connections. Because controller 700 is communicably coupled to the systems and components in systems 100, 200, and/or 400, controller 700 may receive data from one or more of the components shown in FIGS. 1, 2, and/or 4. For example, the data may include oxygen data, fuel flow data, air flow data, and/or temperature data acquired via one or more of the sensors (e.g., temperature sensors, oxygen sensors, flow sensors, etc.).

In general, the routines executed to implement the embodiments may be implemented as part of an operating system or a specific application, module, or sequence of instructions. In certain embodiments, controller 700 includes one or more modules structured to functionally execute the operations to necessary to determine the composition of a gaseous fuel stream. The description herein including modules emphasizes the structural independence of the aspects of a controller and illustrates one grouping of operations and responsibilities of a controller. More specific descriptions of certain embodiments of a controller's operations are described by the sections herein referencing FIGS. 1-6. Other groupings that execute similar overall operations are understood within the scope of the present application. The modules typically comprise one or more instructions set at various times in various memory and storage devices in a computer, and that, when read and executed by one or more processors in a computer, cause the computer to perform operations necessary to execute elements of disclosed embodiments. Moreover, various embodiments have been described in the context of fully functioning computers and computer systems, those skilled in the art will appreciate that the various embodiments are capable of being distributed as a program product in a variety of forms, and that this applies equally regardless of the particular type of computer-readable media used to actually effect the distribution. Examples of computer-readable media include but are not limited to recordable type media such as volatile and non-volatile memory devices, floppy and other removable disks, hard disk drives, optical disks, flash memory, among others.

Example and non-limiting module implementation elements include the sensors, systems, and/or connections required to allow the controllers to determine the composition of gaseous fuel as discussed herein. Any such implementation elements each may be communicably coupled to the controllers and provide any value determined herein. Example and non-limiting module implementation elements may further include devices for providing any value that is a precursor to a value determined herein, data links and/or network hardware including communication chips, oscillating crystals, communication links, cables, twisted pair wiring, coaxial wiring, shielded wiring, transmitters, receivers, and/or transceivers, logic circuits, hard-wired logic circuits, reconfigurable logic circuits in a particular non-transient state configured according to the module specification, any valve actuator including at least an electrical, hydraulic, or pneumatic actuator, a solenoid, an op-amp, analog control elements (springs, filters, integrators, adders, dividers, gain elements), and/or digital control elements.

The schematic flow chart diagrams and method schematic diagrams described above are generally set forth as logical flow chart diagrams. As such, the depicted order and labeled steps are indicative of representative embodiments. Other steps, orderings and methods may be conceived that are equivalent in function, logic, or effect to one or more steps, or portions thereof, of the methods illustrated in the schematic diagrams.

Additionally, the format and symbols employed are provided to explain the logical steps of the schematic diagrams and are understood not to limit the scope of the methods illustrated by the diagrams. Although various arrow types and line types may be employed in the schematic diagrams, they are understood not to limit the scope of the corresponding methods. Indeed, some arrows or other connectors may be used to indicate only the logical flow of a method. For instance, an arrow may indicate a waiting or monitoring period of unspecified duration between enumerated steps of a depicted method. Additionally, the order in which a particular method occurs may or may not strictly adhere to the order of the corresponding steps shown. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in machine-readable medium for execution by various types of processors. An identified module of executable code may, for instance, comprise one or more physical or logical blocks of computer instructions, which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of computer readable program code may be a single instruction, or many instructions, and may even be distributed over several different code segments, among different programs, and across several memory devices. Similarly, operational data tray be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in machine-readable medium (or computer-readable medium), the computer readable program code may be stored and/or propagated on in one or more computer readable medium(s).

The computer readable medium may be a tangible computer readable storage medium storing the computer readable program code. The computer readable storage medium may be, for example, but not limited to, an electronic, magnetic, optical, electromagnetic, infrared, holographic, micromechanical, or semiconductor system, apparatus, or device, or any suitable combination of the foregoing.

More specific examples of the computer readable medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store computer readable program code for use by and/or in connection with an instruction execution system, apparatus, or device.

The computer readable medium may also be a computer readable signal medium. A computer readable signal medium may include a propagated data signal with computer readable program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport computer readable program code for use by or in connection with an instruction execution system, apparatus, or device. Computer readable program code embodied on a computer readable signal medium may be transmitted using any appropriate medium, including but not limited to wireless, wireline, optical fiber cable, Radio Frequency (RF), or the like, or any suitable combination of the foregoing.

In one embodiment, the computer readable medium may comprise a combination of one or more computer readable storage mediums and one or more computer readable signal mediums. For example, computer readable program code may be both propagated as an electro-magnetic signal through a fiber optic cable for execution by a processor and stored on RAM storage device for execution by the processor.

Computer readable program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The computer readable program code may execute entirely on the user's computer, partly on the user's computer, as a stand-alone computer-readable package, partly on the user's computer and partly on a remote computer or entirely on the remote computer or server.

The program code may also be stored in a computer readable medium that can direct a computer, other programmable data processing apparatus, or other devices to function in a particular manner, such that the instructions stored in the computer readable medium produce an article of manufacture including instructions which implement the function/act specified in the schematic flowchart diagrams and/or schematic block diagrams block or blocks.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Accordingly, the present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A system, comprising:
   a pump structured to direct a gaseous fuel stream over a first catalyst at a fuel mass flow rate, wherein the gaseous fuel stream comprises a methane hydrocarbon, non-methane hydrocarbon, and an inert gas;
   a first mass flow control device structured to provide air at a first air mass flow rate to mix into the gaseous fuel stream upstream of the first catalyst;
   the first catalyst positioned to oxidize the non-methane hydrocarbon in the gaseous fuel stream to produce a resultant fuel stream comprising the methane hydrocarbon and the inert gas;
   a second mass flow control device structured to provide air at a second air mass flow rate to mix into the resultant fuel stream downstream of the first catalyst and upstream of a second catalyst;

the second catalyst positioned to oxidize the methane hydrocarbon in the resultant fuel stream to produce an output fuel stream; and a controller structured to determine a composition of the gaseous fuel stream based on the fuel mass flow rate, the first air mass flow rate, and the second air mass flow rate, wherein determining the composition of the gaseous fuel stream includes:

determining a value indicative of the methane hydrocarbon in the gaseous fuel stream;

determining a value indicative of the non-methane hydrocarbon in the gaseous fuel stream; and determining a value indicative of the inert gas in the gaseous fuel stream.

2. The system of claim 1, further comprising a first oxygen sensor positioned to acquire first oxygen data indicative of a presence or an absence of oxygen in the resultant fuel stream, wherein the controller is further structured to control the first mass flow control device to adjust the first air mass flow rate based on the first oxygen data.

3. The system of claim 2, further comprising a second oxygen sensor positioned to acquire second oxygen data indicative of a presence or an absence of oxygen in the output fuel stream, wherein the controller is further structured to control the second mass flow control device to adjust the second air mass flow rate based on the second oxygen data.

4. The system of claim 3, wherein the first oxygen sensor comprises a zirconia based oxygen sensor, and wherein the second oxygen sensor comprises a zirconia based oxygen sensor.

5. The system of claim 1, wherein the first catalyst is maintained at a temperature within a range of 250 to 350 degrees centigrade.

6. The system of claim 5, wherein the second catalyst is maintained at a temperature within a range of 550 to 650 degrees centigrade.

7. The system of claim 1, wherein the gaseous fuel stream is a first gaseous fuel stream that is a portion of a second gaseous fuel stream, the system further comprising an engine structured to combust the second gaseous fuel stream.

8. The system of claim 7, wherein the controller is further structured to control at least one of a fuel-to-air ratio and an ignition timing of the engine based on the composition of the first gaseous fuel stream.

9. An apparatus, comprising:

a first mass flow controller structured to provide air at a first air mass flow rate to mix into a fuel stream upstream of a first catalyst, wherein the fuel stream is directed over the first catalyst at a fuel mass flow rate, and wherein the fuel stream includes a methane hydrocarbon, a non-methane hydrocarbon, and an inert gas;

a second mass flow controller structured to provide air at a second air mass flow rate to mix into the fuel stream downstream of the first catalyst and upstream of a second catalyst; and a master controller communicably and operatively coupled to each of the first mass flow controller and the second mass flow controller, wherein the master controller is structured to determine a composition of the fuel stream including a value indicative of the methane hydrocarbon in the fuel stream, a value indicative of the non-methane hydrocarbon in the fuel stream, and a value indicative of the inert gas in the fuel stream, wherein the determination is based on the fuel mass flow rate, the first air mass flow rate, and the second air mass flow rate.

10. The apparatus of claim 9, further comprising an engine controller structured to control operation of an engine based on the composition of the fuel stream, wherein the fuel stream is a first fuel stream, and wherein the engine is structured to combust a second fuel stream associated with the first fuel stream.

11. The apparatus of claim 9, wherein the first catalyst is positioned to oxidize the non-methane hydrocarbon in the fuel stream to produce a resultant fuel stream comprising the methane hydrocarbon and the inert gas, and wherein the second catalyst is positioned to oxidize the methane hydrocarbon in the resultant fuel stream to produce an output fuel stream.

12. The apparatus of claim 9, wherein the first mass flow controller is further structured to adjust the first air mass flow rate based on first oxygen data indicative of an amount of oxygen downstream of the first catalyst and upstream of the second catalyst, and wherein the second mass flow controller is further structured to adjust the second air mass flow rate based on second oxygen data indicative of an amount of oxygen downstream of the second catalyst.

* * * * *